United States Patent
Bosaeus et al.

(10) Patent No.: US 9,585,795 B2
(45) Date of Patent: Mar. 7, 2017

(54) METHOD FOR DETECTING A LIQUID DISCHARGE TO AN ABSORBENT ARTICLE

(75) Inventors: Mattias Bosaeus, Kållered (SE); Allan Elfström, Deptford, NJ (US); Fredrik Mellbin, Kållered (SE)

(73) Assignee: SCA HYGIENE PRODUCTS AB, Göteborg (SE)

( * ) Notice: Subject to any disclaimer, the term of this patent is extended or adjusted under 35 U.S.C. 154(b) by 0 days.

(21) Appl. No.: 14/368,023

(22) PCT Filed: Dec. 23, 2011

(86) PCT No.: PCT/EP2011/073967
§ 371 (c)(1),
(2), (4) Date: Aug. 13, 2014

(87) PCT Pub. No.: WO2013/091728
PCT Pub. Date: Jun. 27, 2013

(65) Prior Publication Data
US 2014/0350503 A1      Nov. 27, 2014

(51) Int. Cl.
*A61F 13/42* (2006.01)
*A61F 13/84* (2006.01)

(52) U.S. Cl.
CPC ...... *A61F 13/42* (2013.01); *A61F 2013/8491* (2013.01)

(58) Field of Classification Search
CPC ............... A61F 13/42; A61F 2013/424; A61F 2013/8488; A61F 2013/8491
(Continued)

(56) References Cited

U.S. PATENT DOCUMENTS

| | | |
|---|---|---|
| 4,940,464 A | 7/1990 | Van Gompel et al. |
| 6,916,968 B2 | 7/2005 | Shapira et al. |

(Continued)

FOREIGN PATENT DOCUMENTS

| | | |
|---|---|---|
| JP | H06-300723 | 10/1994 |
| JP | H07-063720 | 3/1995 |

(Continued)

OTHER PUBLICATIONS

Smith (Smith, Steven W. The Scientist and Engineer's Guide to Digital Signal Processing. San Diego, CA: California Technical Pub., 1997. Internet Archive Wayback Machine. Web. Jun. 13, 2016. http://dspguide.com/ch7/3.htm).*

(Continued)

*Primary Examiner* — Peter S Vasat
(74) *Attorney, Agent, or Firm* — Drinker Biddle & Reath LLP

(57) ABSTRACT

A method for detecting a liquid discharge event in an absorbent article including a sensor adapted to generate an electrical output signal representative of a degree of wetness of the absorbent article, wherein the electrical output signal is received by a processing unit. The method including the steps of providing reference data over time representative of a liquid discharge; acquiring liquid discharge data over time in form of the electrical output signal; analyzing the liquid discharge data over time in relation to the reference data over time by the processing unit; and detecting a liquid discharge event based on the analysis. Also disclosed is a system for detecting liquid discharge event in an absorbent article including an absorbent article including a sensor being arranged to generate an output signal representative of an electrical property, and a processing unit adapted to process the output signal generated by the sensor of the absorbent article.

18 Claims, 6 Drawing Sheets

(58) Field of Classification Search
USPC .......................................................... 604/361
See application file for complete search history.

(56) References Cited

U.S. PATENT DOCUMENTS

| | | |
|---|---|---|
| 7,250,547 B1 | 7/2007 | Hofmeister et al. |
| 7,977,529 B2 | 7/2011 | Bergman et al. |
| 8,933,293 B2 | 1/2015 | De Bruin et al. |
| 2003/0060789 A1* | 3/2003 | Shapira et al. ............... 604/361 |
| 2005/0156744 A1 | 7/2005 | Pires |
| 2007/0083174 A1* | 4/2007 | Ales et al. ................... 604/361 |
| 2007/0270774 A1* | 11/2007 | Bergman et al. ............. 604/361 |
| 2008/0051745 A1* | 2/2008 | Long et al. ................... 604/361 |
| 2008/0243099 A1 | 10/2008 | Tippey et al. |
| 2010/0168702 A1 | 7/2010 | Ales, III et al. |
| 2011/0263952 A1 | 10/2011 | Bergman et al. |
| 2011/0295619 A1 | 12/2011 | Tough |
| 2012/0186349 A1 | 7/2012 | Inoue |
| 2013/0254141 A1* | 9/2013 | Barda et al. ................... 706/12 |

FOREIGN PATENT DOCUMENTS

| | | |
|---|---|---|
| JP | 2003-090795 | 3/2003 |
| JP | 2006-296566 | 11/2006 |
| JP | 2009-198487 | 9/2009 |
| MX | 2014006953 A | 8/2014 |
| WO | WO 96/14813 A1 | 5/1996 |
| WO | WO 00/00144 A2 | 1/2000 |
| WO | WO 2004/100763 A2 | 11/2004 |
| WO | WO 2006/047815 A1 | 5/2006 |
| WO | WO-2008/075227 A1 | 6/2008 |
| WO | WO 2011/013802 | 2/2011 |
| WO | WO 2011/054045 A1 | 5/2011 |
| WO | WO 2011/156862 A1 | 12/2011 |

OTHER PUBLICATIONS

English-language translation of Japanese Notice of Reasons for Rejection mailed Jul. 13, 2015 issued in corresponding Japanese Patent Application No. 2014-547726 (4 pages).

English-language translation of Russian Decision on Grant dated Nov. 17, 2015 issued in corresponding Russian patent application No. 2014130216 (4 pages).

English-language translation of Japanese Decision of Rejection mailed Feb. 15, 2016 issued in corresponding Japanese Patent Application No. 2014-547726 (3 pages).

\* cited by examiner

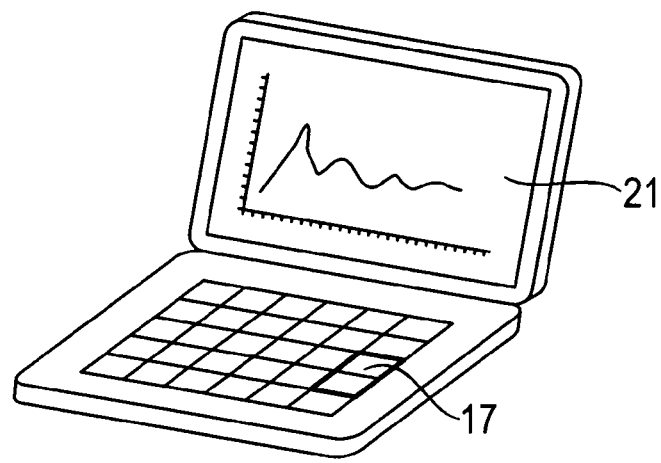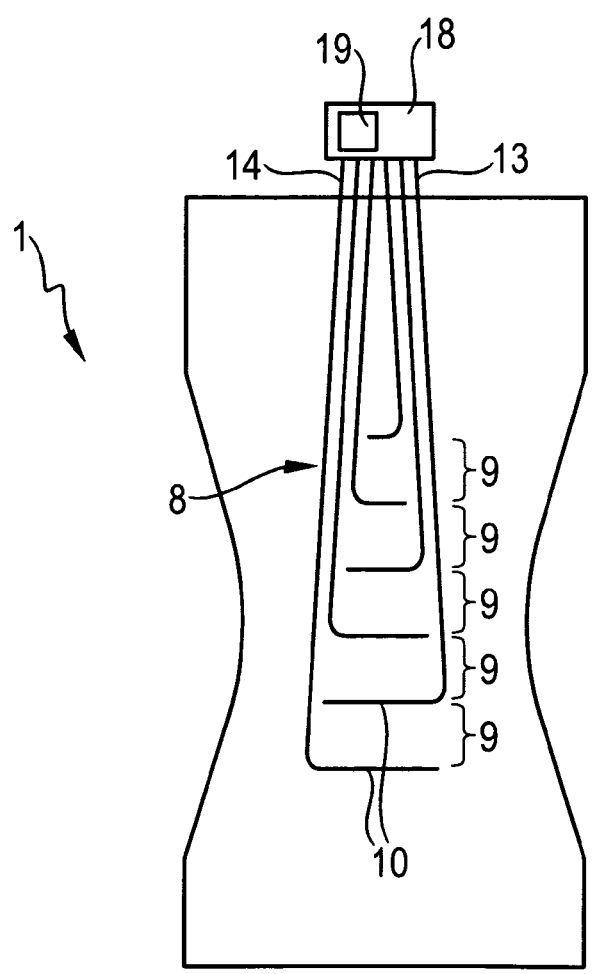
Fig. 5

METHOD FOR DETECTING A LIQUID DISCHARGE TO AN ABSORBENT ARTICLE

CROSS-REFERENCE TO PRIOR APPLICATION

This application is a §371 National Stage Application of PCT International Application No. PCT/EP2011/073967 filed Dec. 23, 2011, which is incorporated herein in its entirety.

TECHNICAL FIELD

Generally, the disclosure relates to a method for detecting liquid discharge to an absorbent article. Further, the disclosure relates to a system suitable for such a method.

TECHNICAL BACKGROUND

Generally, methods for detecting wetness events or liquid discharge to an absorbent article are known in the art. In a conventional system, a sensor monitors a resistance between two conductors arranged in a diaper and compares resistance values to a predetermined and fixed threshold resistance value. If the resistance value is less than the threshold resistance value, then the sensor sends a signal to an alarm device, which informs a caregiver and/or the wearer that the wearer has urinated.

A problem with such a system is that they may be prone to giving false positives, that is informing the caregiver and/or the user that there is urination present in the undergarment when there is not because there is only one "check" or "test" for the presence of micturition (i.e. whether the resistance of the undergarment falls below a fixed threshold value). Such false positives can depend on loose wiring, noise, or disturbances from unknown sources. Further, in certain situations, such as when the person wearing the diaper sits or if other pressure is applied to an undergarment that has been previously wetted, the resistance of the undergarment may fall below the threshold value, thus indicating a new micturition, when in fact a subsequent liquid discharge event has not occurred. Consequently, a false-positive will be detected.

Conventionally, the number of false positive detections is decreased by choosing a higher threshold value. However, a relatively high threshold value increases the risk of non-detection of small amounts of liquid discharge. Accordingly, conventional devices may be ill-suited for accurately detecting multiple micturitions and/or preventing the detection of false-positives. Moreover, sweat may at least somewhat saturate the undergarment, typically over a relatively lengthy period of time, and may trigger the sensor. Still moreover, after a first micturition by the wearer, the resistance value of the undergarment is substantially less than when the product was dry. However, the threshold value has not changed, and therefore, the resistance may be lower than the threshold, thus triggering an alarm, even though a subsequent liquid discharge event has not occurred.

For instance, WO 2008/075227 discloses a method of detecting the presence of a liquid discharge in an absorbent article. In general, a method according to one embodiment of WO 2008/075227 for detecting the presence of a liquid discharge within an absorbent article comprises: monitoring an electrical property of the article as the article is being worn by a wearer, wherein the electrical property changes in response to a liquid discharge; determining a slope in a parameter of the electrical property over time; and comparing the slope to a threshold value to determine the presence of liquid discharge. According to other embodiments of WO 2008/075227 the following can also be determined for detecting a liquid discharge: a comparison of the electrical property over a period of time to a threshold value; and/or a comparison of the electrical property to a determined threshold value.

However, there is still a need of improved methods that at least alleviates the problems of detection of false positives of prior art, allows for reliable detection of multiple micturitions, and is less sensitive for disorders, such as a short circuit of the conductors.

SUMMARY

The present disclosure is based on an insight that by analysing liquid discharge data over time in relation to reference data over time, the accuracy of a method for detecting liquid discharge events can be increased.

A first aspect relates to a method for detecting a liquid discharge event in an absorbent article, wherein said absorbent article includes a sensor adapted to generate an electrical output signal representative of a degree of wetness of said absorbent article, wherein said electrical output signal is received by a processing unit. The method comprising the steps of providing reference data over time representative of a liquid discharge event; acquiring liquid discharge data over time in form of said electrical output signal; analysing said liquid discharge data over time in relation to said reference data over time by means of said processing unit; and detecting a liquid discharge event based on said analysis.

Herein, a degree of wetness is intended to mean any degree of wetness as well as not wet at all, that is, completely dry or other degree of dryness. The degree of wetness can alternatively be expressed as a wetness state. Further, the sensor can be any suitable type of sensor generating an electrical output, which is representative of a wetness state or degree of wetness of the absorbent article. Such a sensor can be a sensor measuring an electrical property such as, conductance, impedance, resistance, admittance, voltage, current, etc. or an electrical property corresponding to temperature, humidity, pH or other suitable property. Further, the sensor can include a semiconductor that is sensitive to urine or wetness. The reference data over time can be a data set, or a mathematical model describing a liquid discharge event, from which a data set over time can be derived. Such a data set can be plotted as a reference curve, if needed or desired. The reference data representative of a liquid discharge event has different characteristics for different types of sensors. Since, the reference data representative of a liquid discharge event has different characteristics for different types of sensors, the reference data need to be determined for the sensor to be used during the method. Further, analysing can include any suitable analysing method for comparing the liquid discharge, or wetness, data and the reference data over time, or for evaluating a difference between the liquid discharge data and the reference data over time. For instance, comparing the liquid discharge data to the reference data over time in some way, or calculating a degree of correlation of the data set and the liquid discharge data. Another suitable method could be curve fitting the liquid discharge data for finding a mathematical function or curve that fits the data and thereafter comparing the fitted curve to a predetermined mathematical function describing the predetermined mathematical model for a liquid discharge or wetness event. Further, still other suitable methods for evaluating degree of conformity or degree of similarity between the liquid discharge data and the reference data could be used.

By analysing the liquid discharge data over time in relation to the reference data over time, the method can take the variation of the data in relation to the reference data over time into consideration, instead of merely comparing an instantaneous liquid discharge data value with a threshold value. In other words, the difference between the characteristics over time of reference data and liquid discharge data is compared, resulting in more reliable liquid discharge detection. Further, the method can take into account a non-linear relationship between the electrical output signal of the sensor and the wetness condition or degree of wetness of the absorbent article.

According to at least one example embodiment, the reference data is predetermined. Herein, predetermined is intended to mean that the data set or the mathematical model is determined before the method is applied. According to at least one example embodiment, the reference data is based on a set of liquid discharge measurements performed prior to applying the method, and, in a particular embodiment, a statistically reliable set of measurements.

According to at least one example embodiment, the step of analysing said liquid discharge data over time in relation to said reference data over time comprises evaluating a degree of conformity of curves representing said liquid discharge data and said reference data over time, respectively, and wherein the step of detecting a liquid discharge event is based on said degree of conformity.

Herein, degree of conformity is intended to mean degree of correspondence in form between the respective curves, representing the two data sets, over time. Degree of conformity and degree of correlation can be evaluated using any suitable method, such as visually comparing the curves, especially their forms, calculating a correlation coefficient, or other known mathematical methods. The degree of conformity can be compared to a predetermined degree of conformity, wherein a liquid discharge is considered to have occurred when the degree of conformity is equal to or higher than the predetermined degree of conformity. The degree of conformity is suitably analysed independently of the actual magnitude of the respective data. In case of multiple liquid discharge events, the degree of conformity is evaluated for each period of time corresponding to one single liquid discharge event.

According to at least one example embodiment, the step of analysing said liquid discharge data over time in relation to said reference data over time comprises evaluating a degree of correlation of said liquid discharge data and said reference data over time, respectively, and wherein the step of detecting a liquid discharge event is based on said degree of correlation.

By evaluating a degree of correlation of said liquid discharge data and said reference data over time, the method can take the variation of the data over time into consideration, instead of comparing with a single threshold value. Thus, more reliable liquid discharge detection is obtained. Degree of correlation can be evaluated using any suitable method, such as visually comparing curves representing liquid discharge data and the reference data, respectively, or calculating a correlation coefficient or other known methods. The degree of correlation can be compared to a predetermined degree of correlation, wherein a liquid discharge is considered to have occurred when the degree of correlation is equal to, higher than, or lower than the predetermined degree of correlation depending on if the correlation is positive or negative. In case of a positive correlation, a liquid discharge is considered to have occurred when the degree of correlation is equal to or higher than the predetermined degree of correlation. And in case of negative correlation, a liquid discharge is considered to have occurred when the degree of correlation is equal to or lower than the predetermined degree of correlation. In case of multiple liquid discharge events, the degree of correlation is evaluated for each period of time corresponding to one single liquid discharge event.

According to at least one example embodiment, the step of analysing said liquid discharge data over time in relation to said reference data over time includes calculating a product of said liquid discharge data and said reference data.

According to at least one example embodiment, the step of analysing said liquid discharge data over time in relation to said reference data over time includes calculating a convolution of said liquid discharge data and said reference data. According to at least one example embodiment, said convolution includes said product.

Herein, a discrete form of convolution is suitable. Such a convolution is advantageous, since it is relatively easy to implement and analyse. Further, using convolution does not require complicated algorithms for shifting the reference data over time to each single liquid discharge event. Alternatively, a cross-correlation could be used instead of a convolution.

According to at least one example embodiment, the step of analysing said liquid discharge data over time in relation to said reference data over time includes comparing the value of the product or the convolution of said data and said reference data to a first predetermined value in relation to a base level of said liquid discharge data, and said step of detecting a liquid discharge event is based on said comparison, wherein a liquid discharge is considered to have occurred when the product or convolution is deviating from said base level by at least said first predetermined value.

The base level is intended to mean a level at which said electrical signal is stable prior to or after a liquid discharge event. That is, either a stable level before any liquid discharge event, or a level to which the signal has stabilized after a liquid discharge event. The deviation can be negative or positive, depending on if the product or correlation is negative or positive. If the product or correlation is positive, a liquid discharge event is considered to have occurred when the product or convolution is deviating positively in relation to a base value with the first predetermined value. If the product or correlation is negative, a liquid discharge event is considered to have occurred when the product or convolution is deviating negatively in relation to a base value with the first predetermined value.

According to at least one example embodiment, the step of analysing said liquid discharge data over time in relation to said reference data over time includes calculating a number of subsequent data values of said product or convolution that are deviating from said base level by said first predetermined value, wherein said number of subsequent data values is compared to a second predetermined value, and wherein a liquid discharge is considered to have occurred when said number of subsequent data values is exceeding the second predetermined value.

Herein, subsequent is intended to mean absolutely subsequent. That is, the subsequent data points are a sequence of data points that are following each other in order. The second predetermined value can be equal to, or different from, the first predetermined value, and is based on the set of liquid discharge measurements performed prior to applying the inventive method.

Such a comparison is advantageous, since it decreases the number of detected false liquid discharge event. Thus, the accuracy of the method is further increased.

According to at least one example embodiment, the sensor includes a plurality of detection zones for detection of liquid discharge and wherein each of said sensor zones is adapted to generate a corresponding electrical output signal representative of a degree of wetness of each respective zone.

The plurality of detection zones can alternatively be in form of a plurality of wetness sensor elements or wetness sensors forming the plurality of detection zones.

According to at least one example embodiment, the step of acquiring liquid discharge data is performed separately for each detection zone.

To acquire data separately for each detection zone is advantageous, since it allows for disregarding data for a desired zone if it includes some kind of errors or inaccuracies.

According to at least one example embodiment, the steps of analysing liquid discharge data and detecting a liquid discharge event are performed for liquid discharge data composed of data for each detection zone, or for data for each detection zone separately.

Herein, composed is intended to mean that the liquid discharge data includes liquid discharge data for each liquid detection zone, for instance in form of a sum of liquid discharge data for each detection zone or in some other suitable way. By performing the steps of analysing liquid discharge data and detecting a liquid discharge event are performed such composed liquid discharge data allows for faster calculations since fewer calculation steps need to be performed. In addition, lower computational requirements are required and memory is required.

According to at least one example embodiment, the step of detecting a liquid discharge event further includes a step of detecting at least one subsequent liquid discharge, based on said data acquired separately for each detection zone, wherein said step of analysing liquid discharge data is applied to the total acquired data over time, or for each part of the acquired data over time corresponding to a single liquid discharge.

According to at least one example embodiment, the method further includes a step of repetitively comparing a change of said electrical output signal representative of a degree of wetness between two different times to a third predetermined value, prior to the step of analysing liquid discharge data, wherein a decision of performing the step of analysing said liquid discharge data is based on said comparison.

Such comparison allows avoiding unnecessary data processing. Therefore, less data capacity is required.

According to at least one example embodiment, the output signal is received by a first processing unit during the step of acquiring liquid discharge data in form of said electrical output signal.

According to at least one example embodiment, the steps of analysing said liquid discharge data in relation to the reference data representative of a liquid discharge and detecting a liquid discharge event based on said analysis, are performed by means of said first processing unit or by means of a second processing unit.

Two processing units allows for data processing at a remote location, which can be advantageous for several reasons. For instance, a unit at the absorbent article can be smaller if it is not configured to process the data. Further, it can be useful for a caregiver to be able to remotely study the liquid discharge data.

According to at least one example embodiment, the electrical output signal is one of resistance, conductance, impedance, voltage, admittance, or current.

A second aspect relates to a system for a detecting liquid discharge event in an absorbent article. The system includes an absorbent article including a sensor being arranged to generate an output signal representative of an electrical property, and a processing unit adapted to process said output signal generated by the sensor of the absorbent article. The processing unit is adapted to perform the method, and detect a liquid discharge event into said absorbent article based on said method.

Suitably, the system is adapted to indicate a liquid discharge event.

According to at least one example embodiment, the system further includes a display unit, which is connected or connectable to said processing unit and arranged to display the result of the method.

According to at least one example embodiment, the system further includes an alarm unit, adapted to generate an alarm signal based on the detection when the liquid discharge event is detected.

The advantages of the system are similar to the advantages of the method, which are described above.

Generally, all terms used in the claims are to be interpreted according to their ordinary meaning in the technical field, unless explicitly defined otherwise herein. All references to "a/an/the element, device, component, means, step, etc." are to be interpreted openly as referring to at least one instance of said element, device, component, means, step, etc., unless explicitly stated otherwise.

Other objectives, features and advantages of the present invention will appear from the following detailed disclosure, from the attached dependent claims as well as from the drawings.

BRIEF DESCRIPTION OF THE DRAWINGS

This and other aspects of the present invention will now be described in more detail, with reference to the appended drawings showing embodiment(s) of the invention, in which:

FIG. 5 illustrates a system for detecting liquid discharge in an absorbent article according to an exemplary embodiment of the invention.

All the figures are highly schematic, not necessarily to scale, and they show only parts which are necessary in order to elucidate the invention, other parts being omitted or merely suggested.

DETAILED DESCRIPTION OF THE DRAWINGS

Herein, words such as upper, lower, below, above etc. are intended to have their ordinary meaning in a vertical direction, when an absorbent article is in use. Thus, an upper portion is a portion that is closer to a user than a lower portion. Further, front and back portions of the absorbent article are intended to mean portions which are at front and back, respectively, in relation to the user, when the absorbent article is in use.

Figure 1:
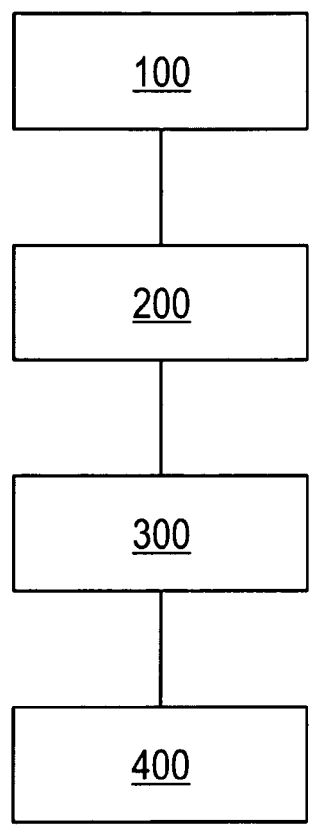
FIG. 1 is a schematic view of a method according to at least a first example embodiment of the present invention.
Figure 6:
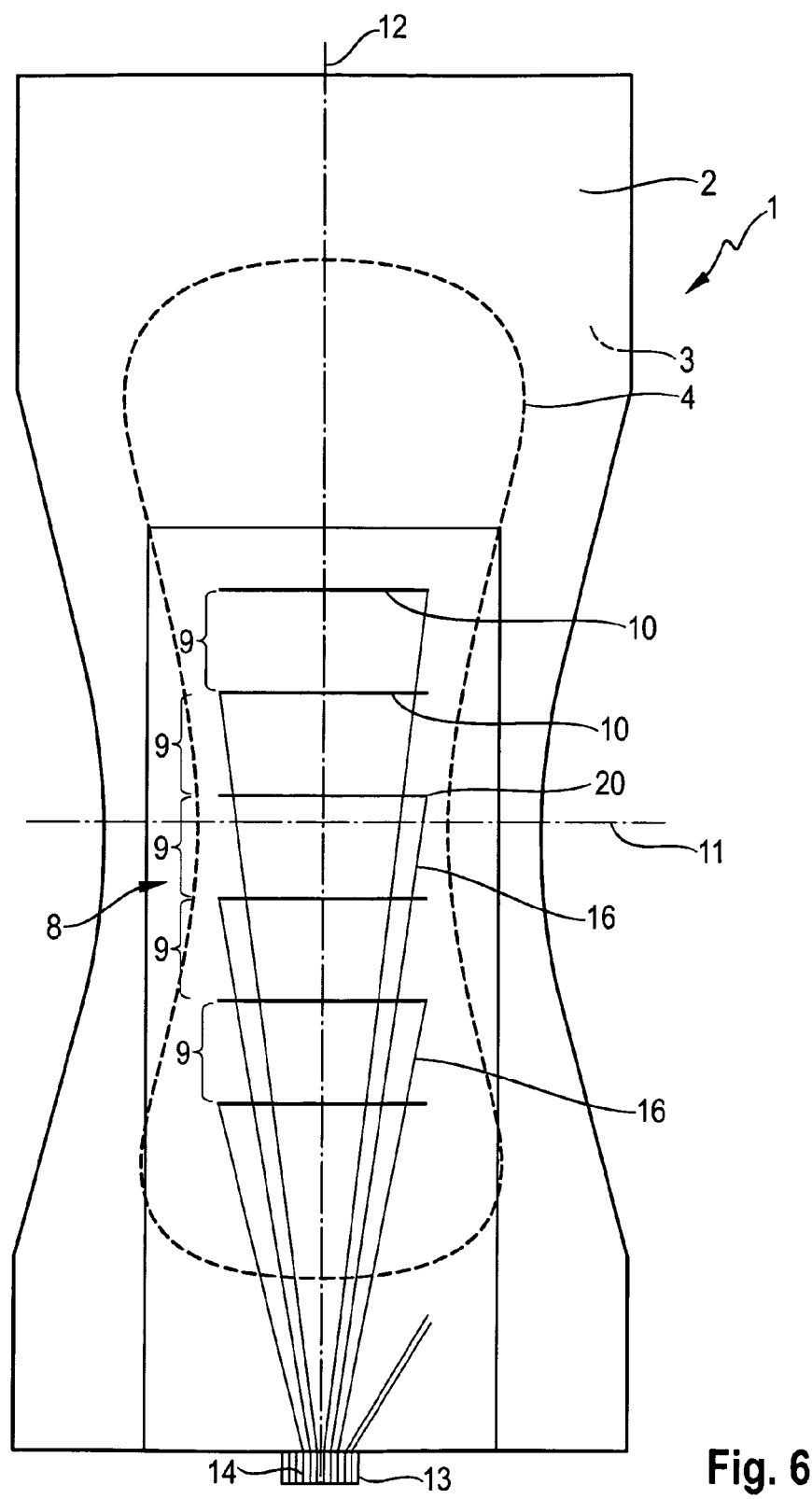
FIG. 6 illustrates schematically an absorbent article suitable for a method and a system according to an embodiment of the invention.

An exemplary embodiment of the method for detecting a liquid discharge event in an absorbent article is illustrated in FIG. 1. In FIG. 6, the absorbent article is in form of an adult incontinence product or diaper 1. The principles disclosed herein are also applicable to other absorbent articles such as baby or toddler diapers, sanitary towels, or other known absorbent articles. The absorbent article 1 includes a sensor adapted to generate an electrical output signal representative of a degree of wetness or a wetness state of said absorbent article, wherein said electrical output signal is received by a processing unit. The method includes the steps of:
   providing 100 predetermined reference data over time representative of a liquid discharge event;
   acquiring 200 liquid discharge data over time in form of said electrical output signal;
   analysing 300 said liquid discharge data over time in relation to reference data over time, representative of a liquid discharge, by means of said processing unit; and
   detecting 400 a liquid discharge based on said analysis.

Suitably, the electrical output signal is one of resistance, conductance, impedance, voltage, admittance, inductance, capacitance, or current. The predetermined reference data is based on a set of pre-performed liquid discharge measurements, that is, performed prior to applying the method to an absorbent article 1. Suitably, the number of pre-performed measurements is such that the set of measurements is statistically reliable. During the pre-performed measurements, liquid is repeatedly discharged to absorbent articles 1 and data is collected. Thereafter, the data is analysed for finding a set of data over time that describes a typical liquid discharge. Suitably, the reference data is in form of a set of discrete data values over time, and can be plotted as a reference curve. A typical set of reference data is illustrated by the reference curve in FIG. 2, which is described in more detail below. Alternatively, a curve fitted to the reference data can describe a typical liquid discharge event. Such a curve can mathematically be described by a function, i.e. a mathematical model describing a liquid discharge event.

During the step of acquiring 200 liquid discharge data in form of said electrical output signal the output signal is received by a first processing unit 19 and the steps of analysing said liquid discharge data in relation to the reference data representative of a liquid discharge event, and detecting a liquid discharge event based on said analysis are performed by means of a second processing unit 17. Alternatively, the steps of analysing 300 said liquid discharge data in relation to the reference data representative of a liquid discharge event, and detecting a liquid discharge event based on said analysis are also performed by means of the first processing unit 19.

The method can also include a step of indicating that a liquid discharge event has occurred. Such indication can be in form of an alarm, by a note in a report, on a display device, or in another suitable form.

In the exemplary embodiment in FIG. 1, the step of analysing 300 liquid discharge data by evaluating conformity of the curves of liquid discharge data and the reference data, respectively, includes calculating a convolution of said liquid discharge data and said reference data. Since the liquid discharge data is in form of discrete values, a discrete form of convolution is suitable. Also, the discrete form of convolution is advantageous, since the discrete form requires less complex analogue electronics.

Generally, the convolution of two functions over a finite range [0,t] is given by:

$$[f*g](t)=\int_0^t f(\tau)g(t-\tau)d\tau.$$

The discrete convolution is given by a sum instead of an integral:

$$[f*g](n) = \sum_0^m f(m)g(n-m).$$

Figure 4:
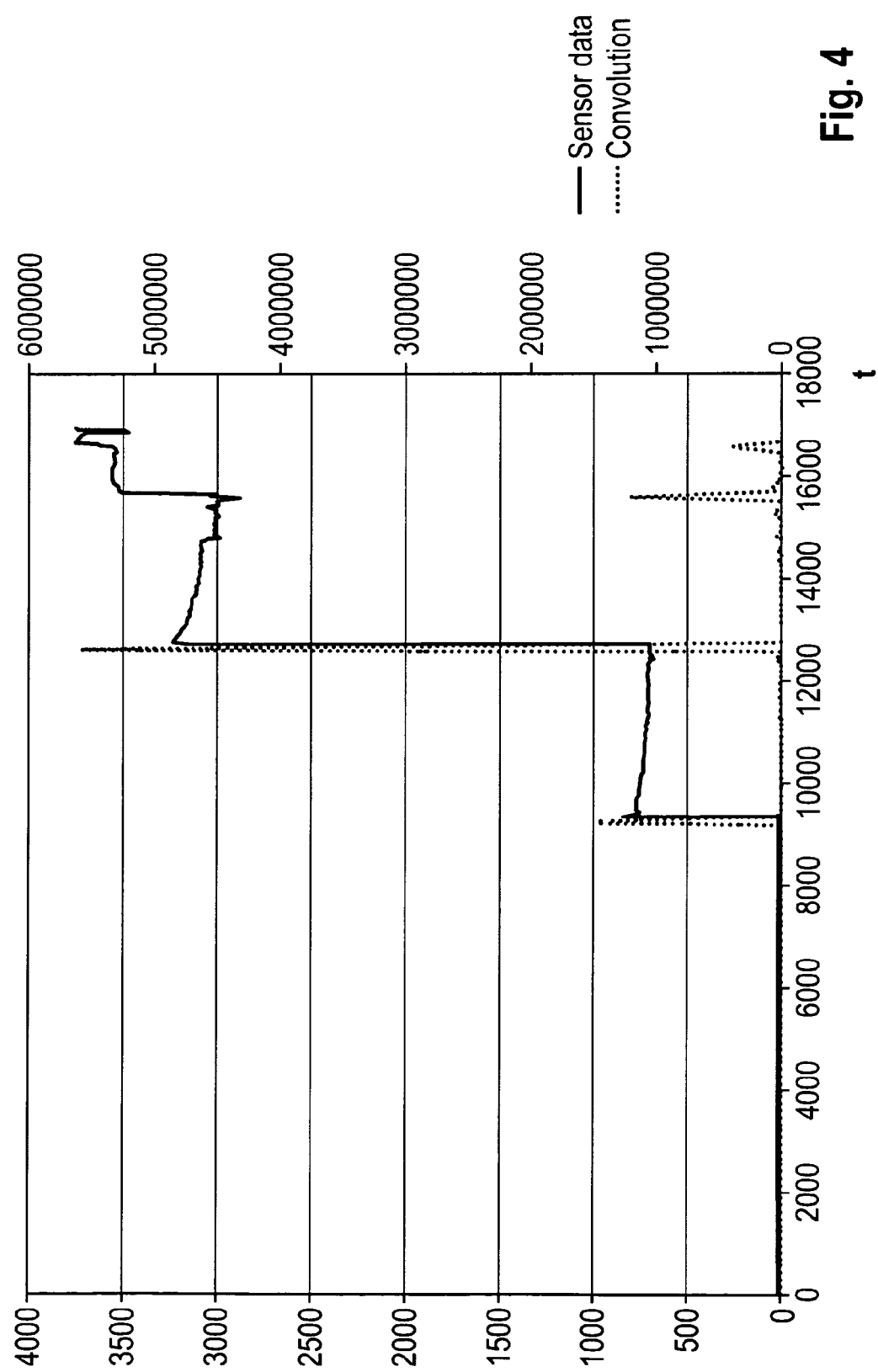
FIG. 4 illustrates liquid discharge data for a plurality of detection zones of the absorbent article and liquid discharges detected by at least one embodiment of the invention.

The resulting discrete convolution is a discrete series with distinctive peaks at the times a liquid discharge has occurred, see FIG. 4. Thereafter, the convolution is compared to a threshold value. If the convolution exceeds the threshold value, which is an example of a deviation by a predetermined value in relation to a base level, a liquid discharge is considered to have occurred and consequently, a liquid discharge event is detected. If instead the continuous integral form of convolution is used, the resulting convolution is a continuous function with peaks at the times a liquid discharge has occurred and a liquid discharge event is detected similarly to the case with the discrete convolution.

By using a convolution, the form of the curve over time representing the liquid discharge data is compared to the form of the curve representing the predetermined reference data, resulting in that the amount of overlap of the two curves, or data sets, is obtained. Consequently, a degree of similarity over time between the liquid discharge and predetermined reference data is calculated. For the discrete convolution, the degree of similarity is a degree of conformity of the data sets plotted as curves. Since the convolution implies that the reference data representative of one liquid discharge event is shifted over the measured liquid discharge data, the convolution can take care of an arbitrary number of liquid discharge events without any additional measures for multiple liquid discharge events. Such additional measures could be manually, or by using an algorithm, shift the reference data repetitively such that the portions of liquid discharge data corresponding to each single liquid discharge event can be compared to the reference data.

If the sensor used to perform the method includes a plurality of detection zones for detection of liquid discharge, each of the sensor zones is adapted to generate a corresponding electrical output signal representative of a degree of wetness or a wetness state of each respective zone. In such a case, the step of acquiring liquid discharge data is suitably performed separately for each detection zone. The liquid discharge data from each of the detection zones can be analysed as liquid discharge data composed of data for each detection zone, suitably as a total sum of each of the zones, or separately. Consequently, also the step of detecting a liquid discharge event is performed for such total liquid discharge data composed of liquid discharge data for each detection zone. Alternatively, the data can be acquired as a sum for all the detection zones together. Still alternatively, the steps of analysing liquid discharge data and detecting a liquid discharge event are performed for data composed of data for each detection zone, or for data for each detection zone separately. Still alternatively, if advantageous the composed data can be in some other suitable form than as a total sum of the data of each detection zone.

In certain embodiments, the method also includes a step of detecting 400 (see FIG. 1) at least one subsequent liquid discharge event, if or whenever present, based on said data acquired separately for each detection zone, wherein said steps of analysing liquid discharge data and detecting a liquid discharge event is applied to the total of acquired data over time. Alternatively, the steps of analysing liquid discharge data and detecting a liquid discharge event can be performed for each part of the acquired data over time corresponding to a single liquid discharge.

In certain embodiments, the method includes a step of repetitively comparing a change of said electrical output signal representative of a degree of wetness between two different times to a predetermined threshold value, prior to the step of analysing liquid discharge data, for deciding if the steps of analysing the liquid discharge data and detecting liquid discharge event should be performed. If the electrical output signal decreases when wetness of the absorbent article increases, the step of analysing is performed when the electrical output signal decreases the predetermined threshold value. On the other hand, if the electrical output signal increases when wetness of the absorbent article increases, the step of analysing is performed when the electrical output signal increases the predetermined threshold value. Such a comparison before analysing data is advantageous, since it decreases unnecessary data analysis, and decreases the required performance of the processor unit.

Figure 2:
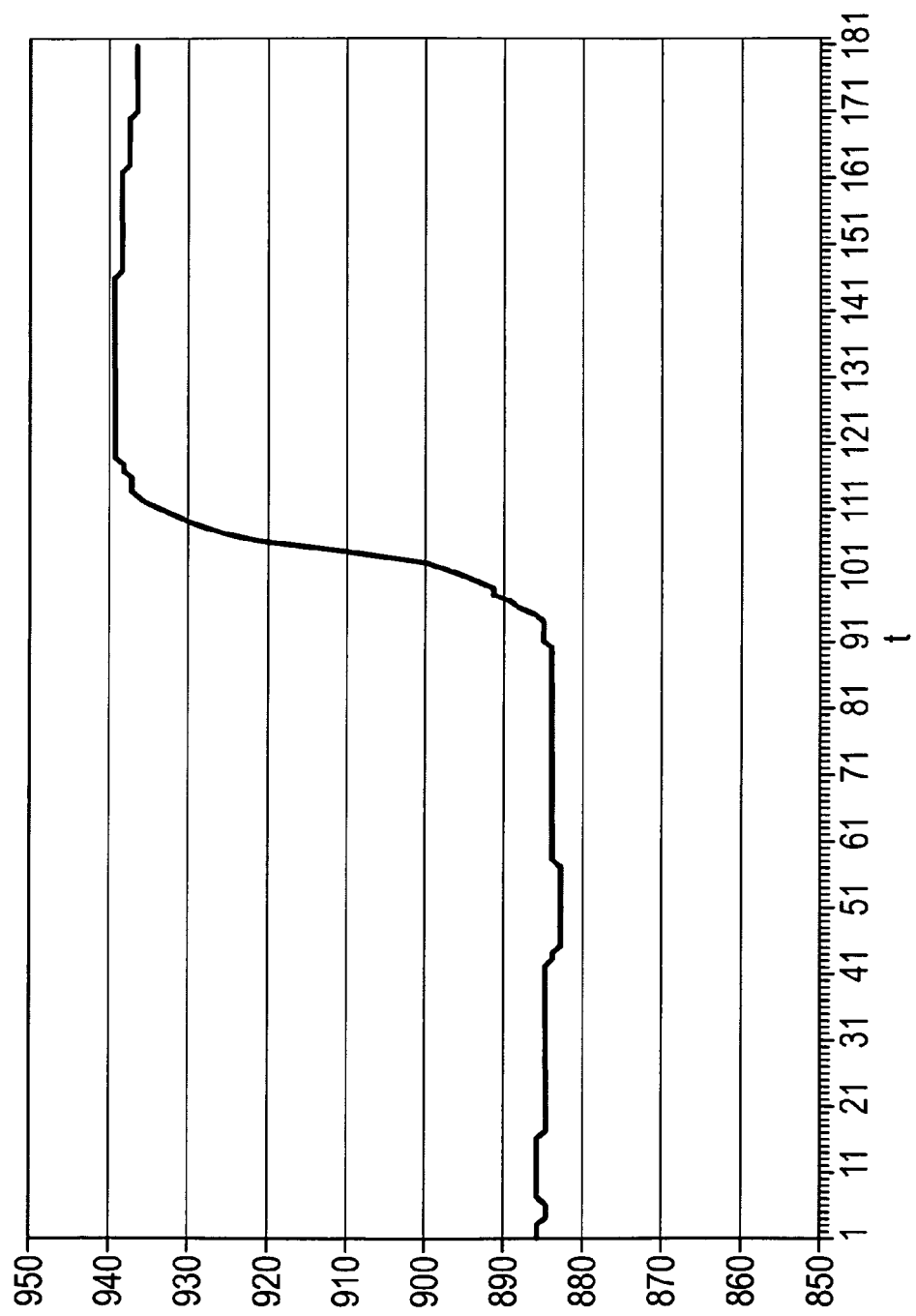
FIG. 2 illustrates a graph of a typical reference data set over time.

FIG. 2 illustrates a graph of a typical predetermined reference data set over time. Generally, if a liquid discharge occurs, the measured electrical property changes. If the measured electrical property is voltage, the lower the measured voltage is, the dryer the absorbent core 4, see FIG. 6. In the case illustrated in FIG. 2, the electrical property increases when liquid discharge is first received in a zone 9, between two adjacent conductive paths 10, and thereafter settles. The electrical property used in the exemplary embodiment is a quotient between a reference resistance and the measured resistance of the absorbent article 1, and therefore, the plotted electrical property is dimensionless. For other electrical properties, the property can instead decrease to a dip or trough, and thereafter settles. Still other sensors can result in reference data with still other characteristics. Subsequent liquid discharge events give rise to subsequent peaks or troughs, depending on the chosen electrical property.

Figure 3:
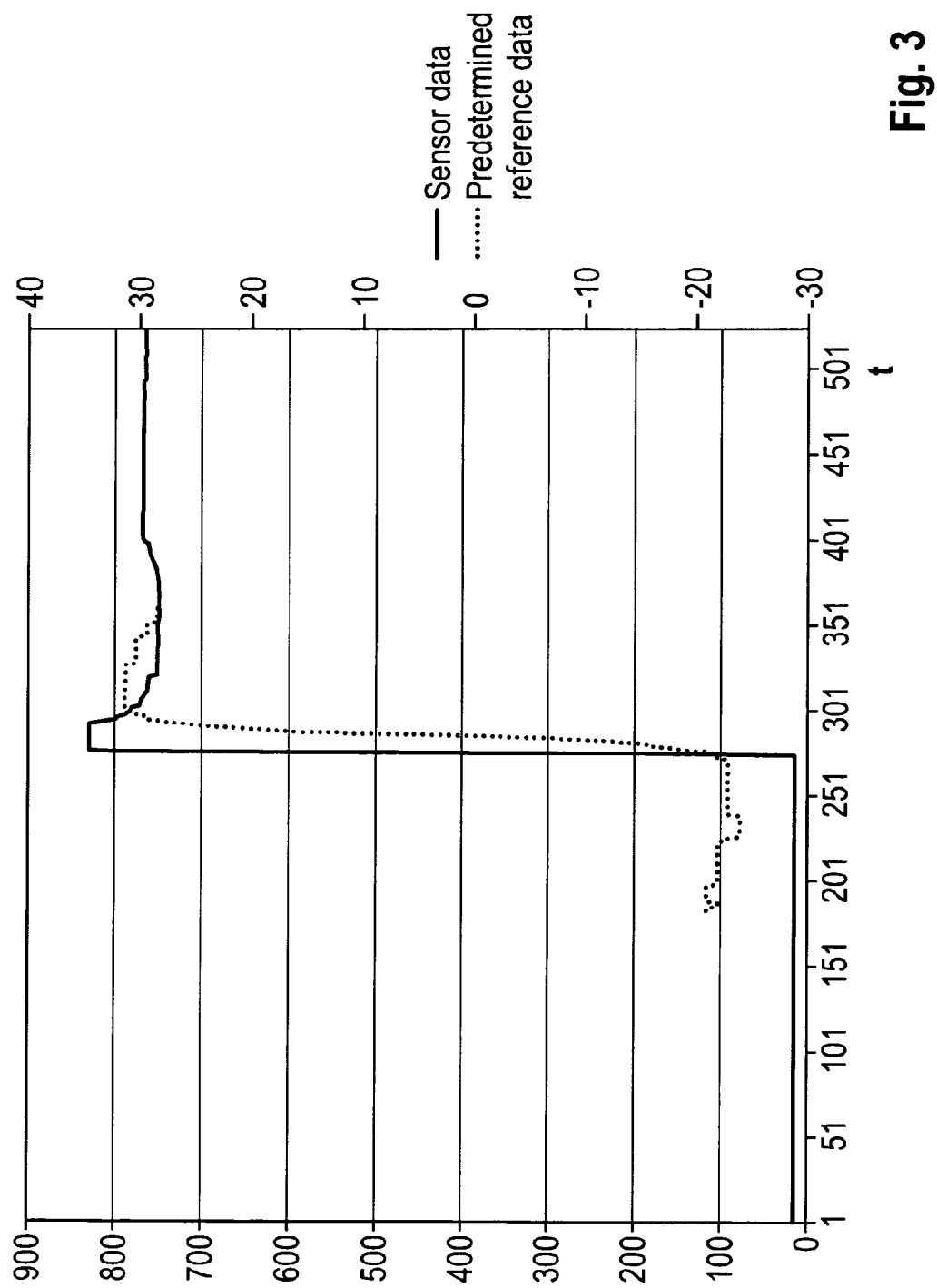
FIG. 3 illustrates liquid discharge data for one zone and a typical reference data set over time.

FIG. 3 illustrates liquid discharge data for one zone of the diaper 1 and a typical reference data set over time. The solid line corresponds to sensor data, while the dotted line corresponds to the reference data. It is clear that the forms of the curves are similar, and therefore the degree of the conformity of the curves is high indicating a liquid discharge event.

FIG. 4 illustrates liquid discharge data for a plurality of detection zones 9 of the absorbent article and liquid discharge events detected by at least one embodiment. The solid line corresponds to sensor data, while the dotted line corresponds to the convolution of the sensor data and the reference data. The sensor data includes a sum over all of the zones 9. The peaks of the convolution of the sensor data and the reference data indicate the times at which a liquid discharge event occurred. In FIG. 4, a first liquid discharge event occurred slightly after t=9000, a second liquid discharge event occurred almost at t=12000, a third liquid discharge event occurred almost at t=16000, and finally a fourth liquid discharge event occurred slightly after t=16000. The second, third, and fourth, liquid discharge events can either have been detected by the same zone 9 as the first liquid discharge event, or by another zone 9 or zones 9. It is clear that the peaks of the convolution of the sensor data and the reference data coincide with each increase in electrical property, indicative of a liquid discharge event, of the sensor data.

For further increasing the detection accuracy of the method the number of subsequent data points exceeding the threshold value can be calculated. Alternatively, if the measured electrical property is negative or if for some reason the convolution of the measured liquid discharge data and reference data is negative, the threshold values will also be negative. In such a case, a value which is lower than the negative threshold value will indicate that a liquid discharge event has occurred, or alternatively the absolute value of the electrical property can be compared to a positive threshold value as is described above.

Instead of analysing data using a convolution as is described above, a cross-correlation could be used. In such a case, the method is, in other aspects, similar to the method described above. Still alternatively, other suitable analysing methods for evaluating a difference between the liquid discharge data and the reference data over time can be used. The difference can be evaluated by calculating the actual difference at each data point and based on this calculating a total difference. Such a total difference can thereafter be compared to a total difference threshold value for detecting a liquid discharge event based on said comparison. Alternatively, the difference can be calculated by comparing the liquid discharge data to the predetermined reference data over time in some way; calculating a degree of correlation of the predetermined data set and the liquid discharge data; curve fitting the liquid discharge data and comparing the fitted curve to a predetermined mathematical function describing the predetermined mathematical model for a wetness event; or other suitable methods for evaluating degree of conformity or degree of similarity between the liquid discharge data and the predetermined reference data. In such a case, the step of detecting a liquid discharge event is based on said degree of conformity or degree of similarity. Degree of conformity is intended to mean degree of correspondence in form between the respective curves, representing the two data sets, over time. Degree of conformity and degree of correlation can be evaluated using any suitable method, such as visually comparing the curves, especially the form of the curves, calculating a correlation coefficient or other known mathematical methods. From FIG. 3 it is clear that the forms of the curves are similar. Thus, the degree of the conformity of the curves is high indicating a liquid discharge event. The degree of conformity can be compared to a predetermined degree of conformity, wherein a liquid discharge is considered to have occurred when the degree of conformity is equal to or higher than the predetermined degree of conformity. The degree of conformity is suitably analysed independently of the actual magnitude of the respective data. In case of multiple liquid discharge events, the degree of conformity is evaluated for each period of time corresponding to one single liquid discharge event.

Alternatively, the step of analysing said liquid discharge data over time in relation to said reference data includes evaluating a degree of correlation of said liquid discharge data and said reference data over time, respectively. In such a case, the step of detecting a liquid discharge event is based on said degree of correlation. Degree of correlation can be evaluated using any suitable method, such as visually comparing curves representing liquid discharge data and the reference data, respectively, or calculating a correlation coefficient or other known methods. The degree of correlation can be compared to a predetermined degree of correlation, wherein a liquid discharge is considered to have occurred when the degree of correlation is equal to, higher than, or lower than the predetermined degree of correlation depending on if the correlation is positive or negative. In case of a positive correlation, a liquid discharge is considered to have occurred when the degree of correlation is equal to or higher than the predetermined degree of correlation. And in case of negative correlation, a liquid discharge is considered to have occurred when the degree of correlation is equal to or lower than the predetermined degree of correlation. In case of multiple liquid discharge events, the degree of correlation is evaluated for each period of time corresponding to one single liquid discharge event.

The System

In FIG. 5, a system for detecting liquid discharge in an absorbent article according to an exemplary embodiment is illustrated. The system includes an absorbent article 1 including a sensor 8 being arranged to generate an output signal representative of an electrical property, and a processing unit 19.

Further, the exemplary embodiment of the system in FIG. 5 includes a control unit. The control unit 18 includes contacts to engage with the contacts 14 of the protruding tab of tape of the absorbent article 1. The control unit 18 includes a memory card to provide hard memory, a memory buffer, a measurement circuit for measuring an electrical property, a clock, a battery, a wireless transmitter, and a processor, which is an example of a processing unit 19. The battery is used to power operation of all of the components of the control unit 18.

The measurement circuit is configured to regularly apply a potential between adjacent pairs of conductive paths 10 of the absorbent article 1 and measure or indicate the impedance there between.

The processor 19 of the control unit 18 can be configured to take the measurement data from the measurement circuit and store it in the buffer until a sequence of a set of measurement data for all of the pairs is stored in the buffer. The processor is further configured to store a clock reading with each set measurement data. The storage of this set of data is repeated regularly (e.g. every second). The processor is configured compare the difference between two adjacent data points during the storage of the data with a predetermined value. If the difference deviates by the predetermined value in relation to a base level, the processor is configured to transfer the data from the buffer memory to a remote memory unit, such as a hard memory of some kind of central computer, for remotely recording data. Alternatively, the data can be written into a memory card, which is removable so that the stored data can be accessed by remotely located analysis software. Still alternatively, the stored data can be accessed by a cable, a USC connection or the like. In such instances, other implementations of the hard memory than a memory card may be used.

The second processing unit 17, which is an example of a further processing unit 17, is suitably located in some kind of central computer and includes software for performing at least a portion of the method. The second processing unit 17 is used to process the stored data into a useful form for performing the steps of analysing and detecting of the method described above. A receiver arranged in the central computer is used to retrieve the data transmitted by the transmitter of the control unit 18. Thereafter, the data is inputted into the second processing unit 17. Suitably, the second processing unit 17 takes the liquid discharge data for each of the detection zones 9 from the memory and runs it through a filter to smoothen the data out so as to present clear increases for when a liquid discharge event has occurred and to soften any noise attributes in the data. Thereafter, the software of the second processing unit 17 will perform the steps of analysing and detecting of the inventive method described above.

Instead of being integrated in a central computer, the second processing unit 17 can be integrated in a cell phone, some kind of handheld computer, etc. Still alternatively, instead of including both a processing unit 19 integrated in the control unit 18 and a remote second processing unit 17 integrated in the central computer, the system can includes the single processing unit 19 integrated into the control unit 18 alone. In such a case, the single processing unit 19 of the control unit 18 is adapted to acquire data as well as to process it. In such a case, the alarm unit is integrated into the control unit 18 as well.

Further, the exemplary embodiment in FIG. 5 includes a display unit 21, which is connected or connectable to the processing unit 17 and arranged to display the result of the method, such as the liquid discharge data in a conveniently readable form or merely the convolution of the liquid discharge data and the reference data. For instance, the data can be in form of a graph of the electrical property, such as voltage with a different line style, (such as colour, dots, etc.) for each of the various zones so that the degree of wetness in each of the zones and its progress over time can be viewed by a user of the analysis software.

Further, the system can include an alarm unit 22, adapted to generate an alarm signal based on the detection of a detected liquid discharge event. The alarm unit 22 is suitably arranged in the central computer.

Alternatively, the liquid discharge data over time could be presented to a user in some way (e.g. a graph having a sufficient time resolution) together with the reference data, such that the user can visually compare the two graphs respective data for detecting each individual liquid discharge.

FIG. 6 illustrates an absorbent article 1 suitable for a method for detecting liquid discharge. Generally, the absorbent article 1 includes a top sheet 2, a back sheet 3 and an absorbent core 4 arranged there between. In use, the top sheet 2 is facing the crotch portion of the user and the back sheet 3 is on the opposite side of the absorbent core 4. In a longitudinal direction, the absorbent article 1 generally includes a front portion, a back portion and a crotch portion arranged there between. In FIG. 1 the absorbent article is shown in form of an adult incontinence diaper 1. The diaper 1, which is illustrated in FIG. 6, is an example of a conventional diaper except for the presence of a wetness sensor 8, including a plurality of liquid discharge detection zones 9 (in this specific example, there are five liquid discharge detection zones 9). The wetness sensor 8 is adapted to generate an electrical output signal representative of a wetness state or degree of wetness of the absorbent core 4 of the diaper 1.

In the exemplary diaper 1 in FIG. 6, each detection zone 9 includes first and second electrically conductive paths 10 (in the form of electrically conductive threads, or other electrically conductive material) that are each aligned with the lateral axis 11 of the absorbent article 1 and are longitudinally spaced from one another along the longitudinal axis 12 of the absorbent article 1. The conductive paths 10 are in physical and electrical contact with the absorbent core 4. The end detection zones 9 share a conductive path 10 with an adjacent zone, while the middle detection zones 9 share both conductive paths 10 with their adjacent detection zones 9.

Further, the absorbent article 1 includes a control unit contact area 13 to which a control unit (not shown) is to be connected in order to activate each of the detection zones 9 to get a liquid discharge reading. The contact area 13 is located at a laterally central front waist region of the absorbent article 1. The contact area 13 includes a plurality of electrical contacts 14 for making electrical contact with corresponding contacts on the control unit. Each conductive path 10 is connected to a respective electrical contact 14 by way of a respective electrically conductive lead 16. The combination of a given contact 14, a lead 16 and a conductive path 10 is formed of a unitary structure (a conductive thread) in at least one exemplary embodiment, as will be made clearer in the following. The leads 16 extend along the shortest path from the conductive path 10 to the corresponding contact 14.

The conductive path 10 can be distinguished from the lead 16 because the conductive path 10 is in direct physical and electrical contact with the absorbent core 4, while the lead 16 is not, so that it can be electrically isolated from the absorbent core 4. More specifically, the conductive paths 10 are on the absorbent core side of the back sheet and in electrical and physical contact with the absorbent core 4. The leads 16 are located on the other side of the back sheet so that the back sheet offers electrical insulation between the absorbent core 4 and the leads 16. The leads 16 each pass through the back sheet at the points 20. One end of each conductive path 10 terminates without a return path to the contact area 13. Accordingly, a return path can only be established by current passing from one contact 14 through one lead 16 and one conductive path 10 and returning through an adjacent conductive path 10 and its lead 16 by current passing across a space between the adjacent conductive paths 10 as a result of the absorbent core 4 becoming wetted in the space.

In one exemplary embodiment, each corresponding contact 14, lead 16 and conductive path 10 are made of a unitary thread that has been coated with electrically conductive material (e.g. metal, carbon, or conductive polymers).

The scope of the invention according to the claims is not limited to the diaper 1 described above or the wetness sensor 8 described above. The principles of the present invention are, however, applicable to other absorbent articles such as baby or toddler diapers, sanitary towels or other known absorbent articles. Further, the principles described above are applicable to other suitable wetness sensors 8 comprising one detection zone 9 or a plurality of detection zones 9 as well. For instance, the conductive paths 10 could instead be implemented by electrically conductive ink printed onto the absorbent article 1 or on a carrier integrated into the article. Still alternatively, instead of an absorbent article including a wetness sensor 8, which includes a plurality of detection zones 9, an absorbent article 1 including a plurality of sensors or sensor elements could be used. In such a case, each sensor corresponds to detection zone 9 described above, and the plurality of detection zones 9 can be considered to be formed by the plurality of sensors or sensor elements. Further, liquid discharge data is analysed as is described above for the sensor including a plurality of detection zones. Still alternatively, the absorbent article 1 can include a combination of a plurality of detectors or sensors (or sensor elements) with a plurality of detection zones.

To use the system described above, a user takes an absorbent article having liquid discharge detection zones 9, suitably in from of a diaper 1 as shown in FIG. 6. The control unit 18 is attached to a front waist region of the absorbent article 1 such that the control unit 18 is connected to the control unit contact area 13 of the absorbent article 1. The absorbent article is mounted to a wearer so that the control unit 18 is able to acquire data concerning liquid discharge events at any given time.

As the control unit and the absorbent article are contacted as described above, the measurement circuit begins to collect data. Thus, the measurement circuit of the control unit 18 will apply for a short duration (less than one tenth of a second) an electric potential between the first and second conductive paths 10 of one of the liquid discharge detection zones 9 and will repeat the operation for each of the liquid discharge detection zones 9 in turn. The electrical potential can be in from of an AC voltage or a DC voltage. The electrical property between the first and second conductive paths 10 in each of the detection zones 9 is taken and stored in the buffer memory. This process is repeated until a difference between two adjacent data points exceeds a predetermined threshold value i.e. is deviating from a base level by the predetermined value, as is explained earlier. At that time, data is transferred to a remote memory at the central computer. Thereafter, data can be collected and transmitted wirelessly to the memory continually in real time. Thereafter, the process of collecting data continues for the lifetime of use of the control unit 18 and the absorbent article.

If the wearer urinates or other type of liquid is discharged, current is able to flow between the first and second conductive paths 10 of the liquid discharge detection zone 9 in which the urination or liquid discharge initially takes place. This will cause a change in the electrical property, that is, for instance in the impedance of the core 4, that can be detected. Consequently, the control unit 18 is able to detect and record a change in an electrical property such as impedance, resistance, conductance, voltage, admittance, current, inductance, capacitance etc. As the urination spreads through the liquid discharge detection zones 9, the electrical property change in the other detection zones 9 can be acquired, i.e. detected and recorded. If certain of the detection zones 9 become saturated, and there is a second urination event, the detection zones 9 that have not yet been saturated or activated will provide a change of electrical property in the output signal for those detection zones 9, which will thus allow the analysis software of the processing unit to pick up on a subsequent liquid discharge event. When data is acquired and recorded the software of the processing unit 17 will perform the method described above for detecting liquid discharge.

Even though the invention has been described with reference to specific exemplifying embodiments thereof, many different alterations, modifications and the like will become apparent for those skilled in the art. For example, additionally, variations to the disclosed embodiments can be understood and effected by the skilled addressee in practicing the claimed invention, from a study of the drawings, the disclosure, and the appended claims. In the claims, the word "comprising" does not exclude other elements or steps, and the indefinite article "a" or "an" does not exclude a plurality. A single unit may fulfil the functions of several items recited in the claims. The mere fact that certain measures are recited in mutually different dependent claims does not indicate that a combination of these measured cannot be used to advantage.

The invention claimed is:

1. A method for detecting a liquid discharge event in an absorbent article, wherein said absorbent article comprises a sensor adapted to generate an electrical output signal representative of a degree of wetness of said absorbent article, wherein said electrical output signal is received by a processing unit, said method comprising the steps of:
- providing reference data obtained via collecting sensor output over a time period, wherein the provided reference data has both a sensor output component and a time component, and wherein the reference data is representative of a liquid discharge event;
- acquiring liquid discharge data over a time period, wherein the acquired liquid discharge data has both a sensor output component and a time component, and wherein the sensor output component is said electrical output signal;
- comparing said acquired liquid discharge data to said provided reference data to determine variations of the acquired liquid discharge data in relation to the provided reference data, wherein comparing comprises convoluting said liquid discharge data with said reference data; and
- detecting a liquid discharge event based on said comparison.

2. The method according to claim 1, wherein said reference data is based on a set of liquid discharge measurements performed prior to applying the method.

3. The method according to claim 1, wherein said convoluting said liquid discharge data with said reference data comprises a product of said liquid discharge data and said reference data.

4. The method according to claim 3, wherein said comparing step comprises comparing the value of the product of said liquid discharge data and said reference data to a first predetermined value in relation to a base level of said liquid discharge data, and said step of detecting a liquid discharge event is based on said comparison, wherein a liquid discharge event is considered to have occurred when the product deviates from said base level by at least said first predetermined value.

5. The method according to claim 3, wherein said comparing step comprises calculating a number of subsequent data values of said product that are deviating from a base level by a first predetermined value, wherein said number of subsequent data values is compared to a second predetermined value, and wherein said step of detecting a liquid discharge event is based on said comparison, wherein a liquid discharge event is considered to have occurred when said number of subsequent data values is exceeding the second predetermined value.

6. The method according to claim 1, wherein said sensor comprises a plurality of detection zones, wherein said sensor is adapted to generate for each detection zone an electrical output signal representative of a degree of wetness corresponding to said detection zone.

7. The method according to claim 6, wherein said step of acquiring liquid discharge data is performed separately for each detection zone.

8. The method according to claim 7, wherein said comparing step and said step of detecting a liquid discharge event are performed for liquid discharge data composed of liquid discharge data for each detection zone, or for liquid discharge data for each detection zone separately.

9. The method according to claim 7, wherein said step of detecting a liquid discharge event further comprises a step of detecting at least one subsequent liquid discharge event, based on said data acquired separately for each detection zone, wherein said comparing step is applied to the total acquired data over time, or for each part of the acquired data over time corresponding to a single liquid discharge event.

10. The method according to claim 1, wherein said method further comprises a step of repetitively comparing a change of said electrical output signal representative of a degree of wetness between two different times to a third predetermined value, prior to the step of analysing liquid discharge data, wherein a decision of performing the comparing step is based on said comparison.

11. The method according to claim 1, wherein said output signal is received by said processing unit during the step of acquiring liquid discharge data in form of said electrical output signal.

12. A method for detecting a liquid discharge event in an absorbent article, wherein said absorbent article comprises a sensor adapted to generate an electrical output signal representative of wetness of said absorbent article, said method comprising:
- providing reference data obtained via collecting sensor output over a time period, wherein the provided reference data has both a sensor output component and a time component, and wherein the reference data is representative of a liquid discharge event;
- acquiring liquid discharge data over a time period by a first processing unit, wherein the acquired liquid discharge data has both a sensor output component and a time component, and wherein the sensor output component is said electrical output signal;
- comparing, by a second processing unit that is remote from the first processing unit, said acquired liquid discharge data to said provided reference data to determine variations of the acquired liquid discharge data in relation to the provided reference data, wherein comparing comprises convoluting said liquid discharge data with said reference data; and
- detecting, by the second processing unit, a liquid discharge event based on said comparison.

13. The method according to claim 1, wherein said electrical output signal is one of resistance, conductance, impedance, voltage, admittance, or current.

14. A system for detecting a liquid discharge event in an absorbent article, said system comprising:
- an absorbent article comprising a sensor being arranged to generate an output signal representative of an electrical property, and
- a processing unit adapted to process said output signal generated by the sensor of the absorbent article,
- wherein said processing unit is adapted to perform the method according to claim 1 and to detect a liquid discharge event in said absorbent article based on said method.

15. The system according to claim 14, wherein said system further comprises a display unit, which is connected or connectable to said processing unit and arranged to display the result of said method.

16. The system according to claim 14, wherein said system further comprises an alarm unit adapted to generate an alarm signal based on the detection when the liquid discharge event is detected.

17. The method according to claim 1, wherein said comparing step comprises comparing the value of the convolution of said liquid discharge data with said reference data to a first predetermined value in relation to a base level of said liquid discharge data, and said step of detecting a liquid discharge event is based on said comparison, wherein a liquid discharge event is considered to have occurred when the convolution deviates from said base level by at least said first predetermined value.

18. The method according to claim 1, wherein said comparing step comprises calculating a number of subsequent data values of said convolution that are deviating from a base level by a first predetermined value, wherein said number of subsequent data values is compared to a second predetermined value, and wherein said step of detecting a liquid discharge event is based on said comparison, wherein a liquid discharge event is considered to have occurred when said number of subsequent data values is exceeding the second predetermined value.

* * * * *